United States Patent
Iizuka et al.

(10) Patent No.: US 6,207,825 B1
(45) Date of Patent: Mar. 27, 2001

(54) METHOD FOR PRODUCTION OF PYRROLIDINONE DERIVATIVES

(75) Inventors: Hajime Iizuka; Hiroshi Nagase; Naruyoshi Mita, all of Chiba (JP)

(73) Assignee: Mitsui Chemicals, Inc. (JP)

( * ) Notice: Subject to any disclaimer, the term of this patent is extended or adjusted under 35 U.S.C. 154(b) by 0 days.

(21) Appl. No.: 09/190,297

(22) Filed: Nov. 13, 1998

(30) Foreign Application Priority Data

Nov. 14, 1997 (JP) ........................................ 9-313784
Nov. 20, 1997 (JP) ........................................ 9-319994

(51) Int. Cl.$^7$ ........................ C07D 401/06; C07D 403/06
(52) U.S. Cl. .................. 540/470; 548/314.7; 548/364.1; 548/518; 544/238; 544/335; 544/372; 546/208; 546/278.4; 540/480; 540/553; 540/602; 540/575
(58) Field of Search ............................... 548/518, 314.7, 548/364.1; 544/335, 372, 238; 546/208, 278.4; 540/480, 470, 553, 575, 602

(56) References Cited

U.S. PATENT DOCUMENTS 5,538,985 * 7/1996 Iizuka et al. ...................... 514/326

* cited by examiner

*Primary Examiner*—John M. Ford
*Assistant Examiner*—Thomas McKenzie
(74) *Attorney, Agent, or Firm*—Burns, Doane, Swecker, & Mathis, L.L.P.

(57) ABSTRACT

A compound represented by the following formula (12) useful as an intermediate for production of drug or agricultural chemical:

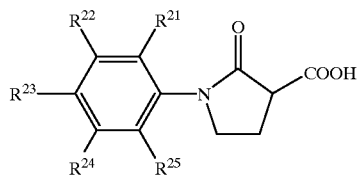

(12)

(wherein $R^{21}$ to $R^{25}$ are each independently a hydrogen atom, a hydroxyl group, a halogen atom, an alkyl group of 1 to 4 carbon atoms, an alkoxy group of 1 to 4 carbon atoms, a perfluoroalkyl group of 1 to 4 carbon atoms, a cyano group, a nitro group, an amino group, a carboxyl group, a thiol group, an alkylthio group of 1 to 4 carbon atoms or a carbamoyl group) can be produced by reacting a compound represented by the formula (13):

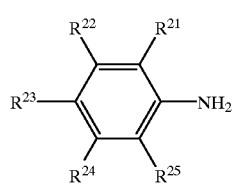

(13)

(wherein $R^{21}$ to $R^{25}$ have the same definitions as given above) with 1,1-cyclopropanedicarboxylic acid. The compound of the formula (12) is useful as a raw material for production of a pyrrolidinone compound useful as an active ingredient of drug.

4 Claims, No Drawings

METHOD FOR PRODUCTION OF PYRROLIDINONE DERIVATIVES

BACKGROUND OF THE INVENTION

1. Field of the Invention

The present invention relates to a process for production of a pyrrolidinone compound which is useful as, for example, a remedy for central nervous system disorders (e.g. schizophrenia, dementia, manic depressive psychosis, anxiety neurosis, drug poisoning and ischemic encephtalopathy), diseases associated with immunodeficiency and cryptorrhea, peptic ulcer, diabetes and complications thereof, glaucoma, etc.; a 3-carboxy-1-substituted-2-pyrrolidinone compound which is a useful intermediate for production of the above pyrrolidinone compound; and a process for production of the 3-carboxy-1-substituted-2-pyrrolidinone compound.

2. Description of the Related Art

Pyrrolidinone compounds having a pyrrolidinone skeleton as the basic structure, which are useful as, for example, a remedy for central nervous system disorders (e.g. schizophrenia, dementia, manic depressive psychosis, anxiety neurosis, drug poisoning and ischemic encephtalopathy), diseases associated with immunodeficiency and cryptorrhea, peptic ulcer, diabetes and complications thereof, glaucoma, etc., and processes for production of the compounds are disclosed in EP Publication No. 0668275A1 and Japanese Patent Application Kokai (Laid-Open) No. 40667/1997.

In producing the pyrrolidinone compounds according to the above processes, however, the number of steps is large and a reduction in the number of steps has been desired for the economic reason. There has also been a problem of using a hydrogen-generating substance. There has also been a problem that a corrosive substance must be used.

With respect to the process for production of a 3-carboxy-1-phenyl-2-pyrrolidinone compound which is useful as an intermediate for production of the above pyrrolidinone compounds, there are known, for example, a process by Danishefsky et al. described in Org. Synth., 60, 66–71, 1981; and a process of hydrolyzing an ester compound obtained by a process described in Japanese Patent Application Kokai (Laid-Open) No. 40667/1997.

However, the former process uses, as a raw material, 6,6-dimethyl-5,7-dioxaspiro[2.5]octane-4,8-dione which is expensive. Also, the latter process of hydrolyzing an ester compound is not preferred for a safety reason because it may use a moisture sensitive/ignitive reagent in synthesis of the ester compound. None of these processes is satisfactory for industrial application.

SUMMARY OF THE INVENTION

An object of the present invention is to provide a process for producing the above pyrrolidinone compound useful as a pharmaceutically active ingredient, wherein the number of steps is smaller and neither hydrogen-generating substance nor corrosive substance is used.

Another object of the present invention is to provide a process for producing a 3-carboxy-1-phenyl-2-pyrrolidinone compound useful as an intermediate for production of the above pyrrolidinone compound useful as a pharmaceutically active ingredient, without using any expensive raw material.

Still another object of the present invention is to provide a process for producing the 3-carboxy-1-phenyl-2-pyrrolidinone without using any moisture sensitive/ignitive reagent.

The pyrrolidinone compound obtained by the present process is represented by the following formula (1):

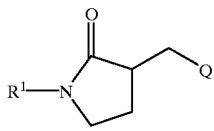
(1)

wherein $R^1$ is an alkyl group of 1 to 12 carbon atoms or a substituent represented by the formula (2):

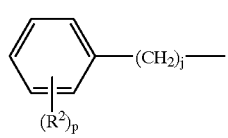
(2)

(wherein R is a hydrogen atom, a halogen atom, an alkyl group of 1 to 4 carbon atoms, an alkoxy group of 1 to 4 carbon atoms, a perfluoroalkyl group of 1 to 4 carbon atoms, a hydroxyl group, a cyano group, an amino group, a nitro group, a carbamoyl group, a thiol group, an alkylthio group of 1 to 4 carbon atoms or a carboxyl group; p is an integer of 1 to 5; when p is 2 or more, each $R^2$ independently has the same definition as given above; and j is an integer of 0 to 2), and Q is a substituent represented by the formula (3a), (3b), (3c) or (3d):

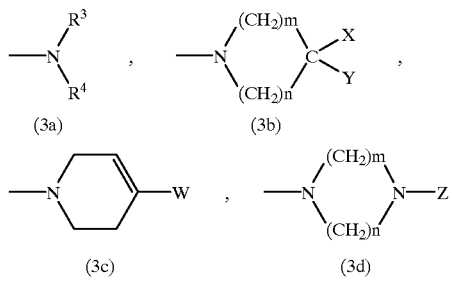

{in the formula (3a), $R^3$ and $R^4$ are each independently a hydrogen atom or an alkyl group of 1 to 4 carbon atoms, and $R^3$ and $R^4$ may bond to each other to form a morpholine ring; in the formula (3b), m and n are each independently an integer of 1 to 4, X is a hydrogen atom, a hydroxyl group, a cyano group, a carbamoyl group, a halogen atom or an alkyl group of 1 to 4 carbon atoms, and Y is a hydrogen atom, an alkyl group of 1 to 4 carbon atoms, a perfluoroalkyl group of 1 to 4 carbon atoms, or a substituted or unsubstituted phenyl group; in the formula (3c), w is an alkyl group of 1 to 4 carbon atoms, a substituted or unsubstituted phenyl group, or an alkyl group of 1 to 2 carbon atoms substituted with a substituted or unsubstituted phenyl group; and in the formula (3d), m and n are each independently an integer of 1 to 4, Z is a hydrogen atom, an alkyl group of 1 to 18 carbon atoms, a substituted or unsubstituted phenyl group, an alkyl group of 1 to 2 carbon atoms substituted with a substituted or unsubstituted phenyl group, or a substituent represented by the formula (4):

—(CH$_2$)$_k$—OR$^5$ (4)

(wherein k is an integer of 2 to 3; and $R^5$ is a hydrogen atom, an alkyl group of 1 to 3 carbon atoms, an alkenyl group of 2 to 3 carbon atoms or an alkynyl group of 2 to 3 carbon atoms)}.

The compound of the formula (1) is useful as, for example, a remedy for central nervous system disorders (e.g. schizophrenia, dementia, manic depressive psychosis, anxiety neurosis, drug poisoning and ischemic encephtalopathy), diseases associated with immunodeficiency and cryptorrhea, peptic ulcer, diabetes and complications thereof, glaucoma, etc.

The present process for producing the pyrrolidinone compound of the formula (1) includes a step of reacting a compound represented by the formula (5):

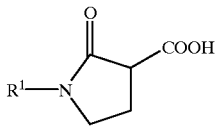

(5)

(wherein $R^1$ has the same definition as given above) with an amine derivative represented by the formula (6a), (6b), (6c) or (6d):

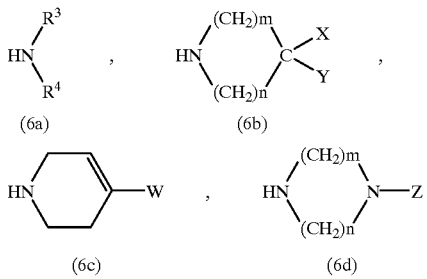

{in the formula (6a), $R^3$ and $R^4$ have the same definitions as given above; in the formula (6b), X, Y, m and n have the same definitions as given above; in the formula (6c), W has the same definition as given above; and in the formula (6d), Z, m and n have the same definitions as given above} in the presence of formaldehyde to produce a pyrrolidinone compound of the formula (1).

The 3-carboxy-1-phenyl-2-pyrrolidinone compound which is useful as a starting material (an intermediate) for production of the pyrrolidinone compound of the formula (1), is represented by the following formula (12) and is one of the compounds of the formula (5):

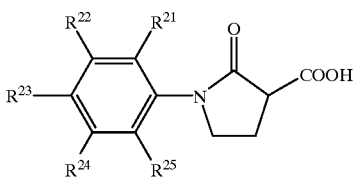

(12)

(wherein $R^{21}$ to $R^{25}$ are each independently a hydrogen atom, a hydroxyl group, a halogen atom, an alkyl group of 1 to 4 carbon atoms, an alkoxy group of 1 to 4 carbon atoms, a perfluoroalkyl group of 1 to 4 carbon atoms, a cyano group, a nitro group, an amino group, a carboxyl group, a thiol group, an alkylthio group of 1 to 4 carbon atoms or a carbamoyl group).

The compound of the formula (12) is useful as an intermediate for production of the pyrrolidinone compound of the formula (1) or as an intermediate for production of an agricultural chemical.

The compound of the formula (12) can be obtained by reacting a compound of the formula (13):

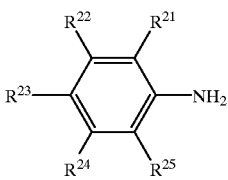

(13)

(wherein $R^{21}$ to $R^{25}$ have the same definitions as given above) with 1,1-cyclopropanedicarboxylic acid.

According to the present invention, there can be provided a process for producing a pyrrolidinone compound of the formula (1), wherein the number of steps is efficiently reduced and neither hydrogen-generating substance nor corrosive substance is used.

According to the present invention, there can also be provided a 3-carboxy-1-phenyl-2-pyrrolidinone compound which is useful as an intermediate for production of the pyrrolidinone compound of the formula (1); and a process for producing the 3-carboxy-1-phenyl-2-pyrrolidinone compound without using any expensive raw material or without using any moisture sensitive/ignitive reagent.

DETAILED DESCRIPTION OF THE INVENTION AND PREFERRED EMBODIMENTS

The production processes of the present invention are described in detail below.

The present process for production of the compound of the formula (1) includes, as mentioned previously, a step of reacting a compound of the formula (5) with one of the compounds of the formulas (6a) to (6d) in the presence of formaldehyde.

Preferably in the present process, a pyrrolidinone compound of the formula (1) {wherein $R^1$ is a substituent represented by the formula (2a):

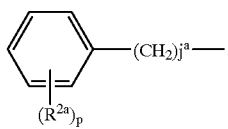

(2a)

(wherein $R^{2a}$ is a hydrogen atom or a halogen atom; p is an integer of 1 to 5; when p is 2 or more, each $R^{2a}$ independently has the same definition as given above; and $j^a$ is 0), and Q is a substituent represented by the formula (7):

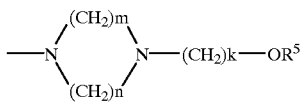

(7)

(wherein m and n are each independently an integer of 1 to 4; k is an integer of 2 to 3; and $R^5$ is a hydrogen atom, an alkyl group of 1 to 3 carbon atoms, an alkenyl group of 2 to 3 carbon atoms or an alkynyl group of 2 to 3 carbon atoms)} is produced by reacting a compound of the formula (5) {wherein $R^1$ is a substituent represented by the formula (2a)

(wherein $R^{2a}$, p and $j^a$ have the same definitions as given above)} with an amine derivative represented by the formula (6d) {wherein Z is a substituent represented by the formula (4) (wherein k and $R^5$ have the same definitions as given above)} in the presence of formaldehyde.

Also preferably in the present process, a pyrrolidinone compound of the formula (1) {wherein $R^1$ is a 4-chlorophenyl group and Q is a substituent represented by the formula (8):

(8)

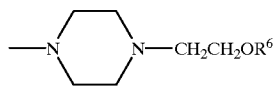

(wherein $R^6$ is an alkyl group of 1 to 3 carbon atoms)} is produced by reacting a compound of the formula (5) (wherein $R^1$ is a 4-chlorophenyl group) with an amine derivative represented by the formula (9);

(9)

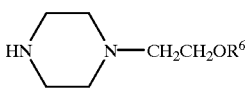

(wherein $R^6$ has the same definition as given above) in the presence of formaldehyde.

The amine derivative represented by the formula (9) is preferably an amine derivative of the formula (9) wherein $R^6$ is a methyl group.

In the general formula (1), "alkyl group of 1 to 3 carbon atoms" refers to a methyl group, an ethyl group, an n-propyl group or an isopropyl group; "alkyl group of 1 to 4 carbon atoms" refers to each group mentioned above, an n-butyl group, a sec-butyl group, a tert-butyl group, an isobutyl group or the like; "alkyl group of 1 to 12 carbon atoms" refers to each group mentioned above, a pentyl group, a hexyl group, a heptyl group, an octyl group, a nonyl group, a decyl group, an undecyl group, a dodecyl group or the like; "alkyl group of 1 to 18 carbon atoms" refers to each group mentioned above, a tridecyl group, a tetradecyl group, a pentadecyl group, a hexadecyl group, a heptadecyl group, an octadecyl group or the like; "alkenyl group of 2 to 3 carbon atoms" refers to a vinyl group, an allyl group, a 1-propenyl group, an isopropenyl group or the like; "alkynyl group of 2 to 3 carbon atoms" refers to an ethynyl group, a 1-propynyl group, a 2-propynyl group or the like; "halogen atom" refers to a fluorine atom, a chlorine atom, a bromine atom or an iodine atom; "alkoxy group of 1 to 4 carbon atoms" refers to a methoxy group, an ethoxy group, an n-propoxy group, an isopropoxy group, a butoxy group or the like; "perfluoroalkyl group of 1 to 4 carbon atoms" refers to a trifluoromethyl group, a pentafluoroethyl group, a heptafluoropropyl group, a nonafluorobutyl group or the like; "alkylthio group of 1 to 4 carbon atoms" refers to a methylthio group, an ethylthio group, a propylthio group, a butylthio group or the like; "substituted phenyl group" refers to a phenyl group substituted with a halogen atom(s), an alkyl group(s) of 1 to 4 carbon atoms, an alkoxy group(s) of 1 to 4 carbon atoms, a perfluoroalkyl group(s) of 1 to 4 carbon atoms or the like; and "alkyl group of 1 to 2 carbon atoms substituted with a phenyl group" refers to a benzyl group, a phenethyl group or the like.

The production route of the present invention for the compound of the formula (1) is shown by the following reaction formula (1).

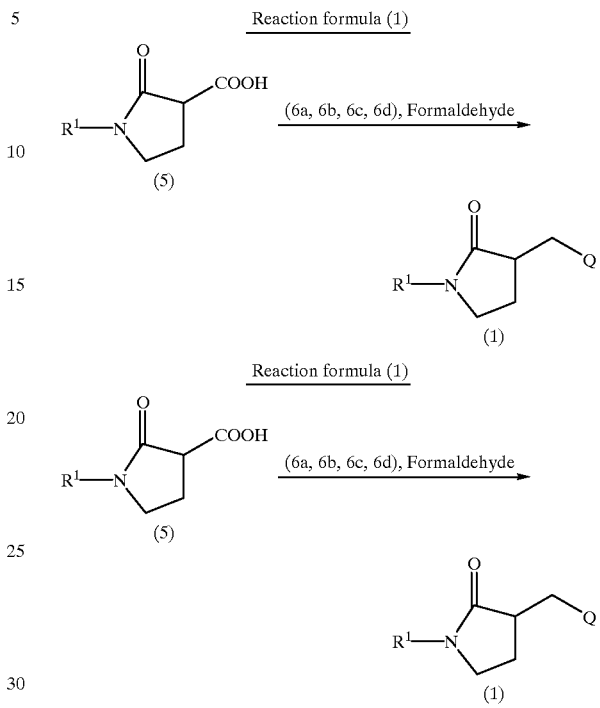

{wherein $R^1$ and Q have the same definitions as in the general formula (1); and 6a, 6b, 6c and 6d have the same definitions as in the general formulas (6a) to (6d)}.

As the formaldehyde used in the reaction of the reaction formula (1), there can be mentioned paraformaldehyde, trioxane, aqueous solutions thereof, etc. The aqueous solution ordinarily has a concentration of 5 to 50% by weight. The formaldehyde is used in an amount of 1 to 10 moles per mole of the compound of the general formula (5).

As the solvent used in the reaction, there can be mentioned water; alcohols such as methanol, ethanol, isopropanol, butanol and the like; ethers such as diethyl ether, dioxane, tetrahydrofuran, ethylene glycol dimethyl ether and the like; aromatic hydrocarbons such as benzene, toluene and xylene and the like; halogen-containing hydrocarbons such as dichloromethane, dichloroethane, chloroform and the like; acetonitrile; and so forth. These solvents can be used singly or in admixture. The reaction may be conducted without using any solvent.

The reaction temperature may range from 0° C. to the boiling point of the solvent used, preferably from room temperature to 150° C.

The reaction time is not particularly restricted, but is preferably 1 to 48 hours.

There is no particular restriction as to the order of mixing the compound of the general formula (5), the amine derivative of the general formula (6a), (6b), (6c) or (6d) and formaldehyde. They are mixed at one time; or, the amine and formaldehyde are mixed first and then the compound of the general formula (5) is added; or, the compound of the general formula (5) and formaldehyde are mixed first and then the amine is added.

In the reaction of the reaction formula (1), there is a case when a 3-methylene form of the compound of the formula (5), represented by the following general formula (10)

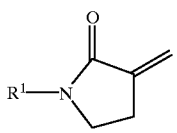

(10)

{wherein $R^1$ has the same definition as in the general formula (1)} is formed as an intermediate. This intermediate may be reacted with the amine of the general formula (6a), (6b), (6c) or (6d).

This reaction may be conducted in an equimolar ratio. The amine may be used in excess.

As the solvent used in the reaction, there can be mentioned water; alcohols such as methanol, ethanol, isopropanol, butanol and the like; ethers such as diethyl ether, dioxane, tetrahydrofuran, ethylene glycol dimethyl ether and the like; aromatic hydrocarbons such as benzene, toluene and xylene and the like; halogen-containing hydrocarbons such as dichloromethane, dichloroethane, chloroform and the like; ketones such as acetone, methyl ethyl ketone and the like; acetonitrile; and so forth. These solvents can be used singly or in admixture. The reaction may be conducted without using any solvent.

The reaction temperature may range from 0° C. to the boiling point of the solvent used, preferably from room temperature to 150° C.

The reaction time is not particularly restricted, but is preferably 1 to 48 hours.

In the post-treatment after the above reaction, a purification method ordinarily used, such as column chromatography, recrystallization or the like can be used.

The compound of the formula (5) is preferably a compound of the formula (5) wherein $R^1$ is represented by the formula (2) (wherein $R^2$ and p have the same definitions as given above, and j is 0), or a salt thereof; more preferably a compound of the formula (5) wherein $R^1$ is a 4-chlorophenyl group.

The compound of the formula (5) can be obtained by a known process, for example, by hydrolyzing, with an acid or an alkali, a compound of the general formula (11)

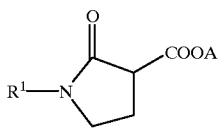

(11)

(wherein $R^1$ has the same definition as in the formula (1), and A is an alkyl group of 1 to 4 carbon atoms, a substituted or unsubstituted phenyl group, or an alkyl group of 1 to 2 carbon atoms substituted with a substituted or unsubstituted phenyl group), the compound of the formula (11) being obtained by a process described in EP Publication No. 0668275A1 or Japanese Patent Application Kokai (Laid-Open) No. 40667/1997.

In the above reaction, there can ordinarily be used, as the acid, an inorganic acid such as hydrochloric acid, sulfuric acid, phosphoric acid or the like; and there can be mentioned, as the alkali, sodium hydroxide, potassium hydroxide, lithium hydroxide, sodium carbonate, potassium carbonate, etc.

The amount of the acid or alkali used is 0.1 to 100 moles, preferably 1 to 10 moles per mole of the compound of the formula (11).

The reaction may be conducted in the presence of a phase-transfer catalyst.

As the solvent used in the reaction, there can be mentioned water; alcohols such as methanol, ethanol, isopropanol, butanol and the like; ethers such as diethyl ether, dioxane, tetrahydrofuran, ethylene glycol dimethyl ether and the like; aromatic hydrocarbons such as benzene, toluene and xylene and the like; halogen-containing hydrocarbons such as dichloromethane, dichloroethane, chloroform and the like; acetonitrile; and so forth. These solvents can be used singly or in admixture.

The reaction temperature may range from 0° C. to the boiling point of the solvent used, preferably from room temperature to 150° C.

The reaction time is not particularly restricted, but is preferably 1 to 48 hours.

The carboxylic acid obtained can be used in the next reaction as it is or in the form of a salt thereof.

A compound of the following formula (12) as one of the compounds of the formula (5):

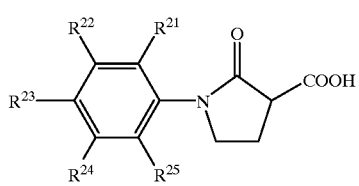

(12)

(wherein $R^{21}$ to $R^{25}$ are each independently a hydrogen atom, a hydroxyl group, a halogen atom, an alkyl group of 1 to 4 carbon atoms, an alkoxy group of 1 to 4 carbon atoms, a perfluoroalkyl group of 1 to 4 carbon atoms, a cyano group, a nitro group, an amino group, a carboxyl group, a thiol group, an alkylthio group of 1 to 4 carbon atoms or a carbamoyl group) can be obtained by reacting a compound represented by the formula (13):

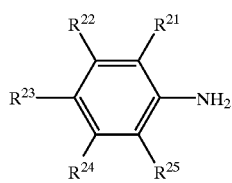

(13)

{wherein $R^{21}$ to $R^{25}$ have the same definitions as in the formula (12)} with 1,1-cyclopropanedicarboxylic acid.

This process, as compared with the known process mentioned above, has a merit in using neither expensive raw material nor moisture sensitive/ignitive reagent.

In the above process, it is preferred that $R^{21}$, $R^{22}$, $R^{24}$ and $R^{25}$ are each a hydrogen atom and $R^{23}$ is a chlorine atom or a bromine atom; and it is more preferred that $R^{21}$, $R^{22}$, $R^{24}$ and $R^{25}$ are each a hydrogen atom and $R^{23}$ is a chlorine atom.

In the formulas (12) and (13), the halogen atom includes a fluorine atom, a chlorine atom, a bromine atom and an iodine atom.

As the lower alkyl group of 1 to 4 carbon atoms, there can be mentioned, for example, a methyl group, an ethyl group, an n-propyl group, an isopropyl group, an n-butyl group, an isobutyl group, a sec-butyl group and a tert-butyl group.

As the lower alkoxy group of 1 to 4 carbon atoms, there can be mentioned, for example, a methoxy group, an ethoxy group a propoxy group, an isopropoxy group, an n-butoxy group, an isobutoxy group, a sec-butoxy group and a tert-butoxy group.

As the perfluoroalkyl group of 1 to 4 carbon atoms, there can be mentioned, for example, a trifluoromethyl group, a pentafluoroethyl group, a heptafluoropropyl group, a heptafluoroisopropyl group and a nonafluorobutyl group.

As the lower alkylthio group of 1 to 4 carbon atoms, there can be mentioned, for example, a methylthio group, an othylthio group, an n-propylthio group, an isopropylthio group, an n-butylthio group, an isobutylthio group, a sec-butylthio group and a tert-butylthio group.

The reaction of the compound of the formula (13) with 1,1-cyclopropanedicarboxylic acid can be conducted in the presence or absence of a solvent. As the solvent, there can be mentioned aromatic hydrocarbons such as benzene, toluene, xylene and the like; ethers such as diethyl ether, tetrahydrofuran, 1,4-dioxane, 1,2-dimethoxyethane, ethylene glycol dimethyl ether and the like; alcohols such as methanol, ethanol, propanol and the like; aprotic polar solvents such as dimethylformamide, dimethyl sulfoxide and the like; halogen-containing solvents such as methylene chloride, chloroform, dichloroethane and the like; carboxylic acid esters such as ethyl acetate, ethyl propionate and the like; carboxylic acids such as formic acid, acetic acid, propionic acid and the like; water; acetone; methyl ethyl ketone; and acetonitrile. These solvents can be used singly or in admixture.

The proportions of the compound of the formula (13) and 1,1-cyclopropanedicarboxylic acid should be determined in view of their reactivity, the formation of by-products and the economy of the reaction; however, the compound of the formula (13) is used in an amount of generally 0.1 to 10 moles, preferably 0.3 to 3 moles, more preferably 0.6 to 1.5 moles per mole of 1,1-cyclopropanedicarboxylic acid.

The reaction temperature, when a solvent is used, may range from about room temperature to the reflux temperature, preferably from 60° C. to 100° C., more preferably from 70° C. to 95° C. and, when no solvent is used, may range from about room temperature to about the melting point of reaction substrates used.

EXAMPLES

The present invention is described more specifically below with reference to Examples. However, the present invention is not restricted by these Examples.

Example 1
Production of 3-carboxy-1-(4-chlorophenyl)-2-pyrrolidinone 2.0 g of 1,1-cyclopropanedicarboxylic acid and 2.9 g of 4-chloroaniline were added to 2.7 g of water. The mixture was stirred at 80° C. for 20 hours.

To the reaction mixture were added 20 ml of a 25% aqueous NaOH solution and 20 ml of ethyl acetate, followed by thorough stirring. The aqueous layer was washed with ethyl acetate and then made acidic with hydrochloric acid. The resulting crystals were collected by filtration, then washed with water, and dried to obtain 2.2 g of an intended compound at a yield of 59.7%.

Melting point: 170° C. (decomposed);
$^1$H-NMR (DMSO, δ ppm): 2.2–2.4 (2H,m), 3.61 (1H,t), 3.8–3.95 (2H,m), 7.4–7.5 (2H,m), 7.65–7.75 (2H,m).

Example 2
Production of 1-(4-bromophenyl)-3-carboxy-2-pyrrolidinone 30 g of 1,1-cyclopropanedicarboxylic acid and 50 g of 4-bromoaniline were added to 50 ml of acetonitrile, followed by refluxing for 7 hours with heating and stirring.

The reaction mixture was subjected to solvent removal under reduced pressure. To the residue were added an aqueous sodium hydrogencarbonate solution and ethyl acetate, and the mixture was stirred thoroughly. The aqueous layer was washed with ethyl acetate, then made acidic with hydrochloric acid, and subjected to extraction with ethyl acetate. The organic layer was dried over anhydrous magnesium sulfate and then concentrated under reduced pressure. The resulting concentrate was sludged with diethyl ether to obtain 32.8 g of an intended compound at a crude yield of 50.2%.

$^1$H-NMR (CDCl$_3$, δ ppm): 2.39–2.68 (2H,m), 3.66 (1H,t), 3.85 (2H,m), 7.51 (4H,s).

Example 3
Production of 3-carboxy-1-(3-trifluoromethylphenyl)-2-pyrrolidinone 10.0 g of 1,1-cyclopropanedicarboxylic acid and 12.4 g of 4-trifluoromethylaniline were added to 15 ml of acetonitrile, followed by refluxing for 7 hours with heating and stirring. The subsequent operation was conducted in the same manner as in Example 2 to obtain 7.1 g of an intended compound at a yield of 38.8%.

$^1$H-NMR (CDCl$_3$, δ ppm): 2.43–2.67 (2H,m), 3.73 (1H,t), 3.97 (2H,t), 7.47–7.54 (2H,m), 7.75–7.87 (2H,m).

Reference Example 1
Production of 3-carboxy-1-(4-chlorophenyl)-2-pyrrolidinone 61.8 g of 1-(4-chlorophenyl)-3-ethoxycarbonyl-2-pyrrolidinone was mixed with 45 g of ethanol. Thereto was added a solution of 46.1 g of sodium hydroxide dissolved in 100 ml of water, followed by mixing. The mixture was once made into a complete solution, after which a large amount of crystals appeared.

Thereto was added water. The crystals were collected by filtration and washed with diethyl ether. To the filtrate was added diethyl ether, followed by stirring. The aqueous layer was separated. This aqeuous layer and the crystals were combined and made acidic with hydrochloric acid with thorough stirring. The crystals were collected by filtration and washed with water to obtain 52.5 g of 3-carboxy-1-(4-chlorophenyl) -2-pyrrolidinone.

Melting point: 170° C. (decomposed);
$^1$H-NMR (DMSO, δ ppm): 2.2–2.4 (2H,m), 3.61 (1H,t), 3.8–3.95 (2H,m), 7.4–7.5 (2H,m), 7.65–7.75 (2H,m).

This spectrum data corresponded with that of the compound obtained by reacting p-chloroaniline with 6,6-dimethyl-5,7-dioxyaspiro[2,5]octane-4,8-dione according to the method described in Org. Synth., 60, 66–71, 1981.

Example 4
Production of 1-(4-chlorophenyl)-3-[4-(2-methoxyethyl) piperazine-1-yl]methyl-2-pyrrolidinone 3.0 g of 1-(4-chlorophenyl)-3-carboxy-2-pyrrolidinone and 2.32 g of 4-(2-methoxyethyl)piperazine were mixed with 6 ml of methanol. Thereto was added 0.465 g of 80% paraformaldehyde. The mixture was subjected to a reaction for 10.5 hours under refluxing and then cooled to room temperature. Thereto was added 10 ml of methanol, and the insolubles were removed by filtration. The filtrate was concentrated under reduced pressure. The residue was mixed with 15 ml of water. The resulting crystals were collected by filtration and washed with 3 ml of 95% aqueous methanol twice to obtain 3.42 g of 1-(4-chlorophenyl)-3-[4-(2-methoxyethyl)piperazine-1-yl]methyl-2-pyrrolidinone.

Melting point: 103–105° C.;
$^1$H-NMR (CDCl$_3$, δ ppm): 2.01–2.12 (1H,m), 2.29–2.62 (12H,m), 2.78–2.94 (2H,m), 3.35 (3H,s), 3.51 (2H,t), 3.74–3.80 (2H,m), 7.32 (2H,d), 7.59 (2H,d).

Reference Example 2
Production of 1-(4-chlorophenyl)-3-methylene-2-pyrrolidinone 1.56 g of 1-(4-chlorophenyl)-3-carboxy-2-pyrrolidinone was mixed with 7 ml of methanol. Thereto were added 0.26 g of 75% paraformaldehyde and 0.75 g of 4-methoxypiperidine. The mixture was refluxed for 2 hours. The reaction mixture was concentrated to dryness. The residue was purified by silica gel column chromatography using chloroform (a solvent) to obtain 0.85 g of 1-(4-chlorophenyl)-3-methylene-2-pyrrolidinone.

Melting point: 119–120° C.;
$^1$H-NMR (CDCl$_3$, δ ppm): 2.87–2.94 (2H,m), 3.83 (2H,t), 5.46 (1H,t), 6.14 (1H,t), 7.32–7.37 (2H,m), 7.67–7.73 (2H, m).

Reference Example 3
Production of 1-(4-chlorophenyl)-3-[4-(2-methoxyethyl)piperazine-1-yl]methyl-2-pyrrolidinone 0.85 g of 1-(4-chlorophenyl)-3-methylene-2-pyrrolidinone and 0.71 g of 4-(2-methoxyethyl)piperazine were mixed with 3 ml of acetonitrile. The mixture was refluxed for 3.5 hours. The reaction mixture was concentrated to dryness. The residue was purified by silica gel column chromatography using a mixed solvent (chloroform/methanol=20/1) to obtain 1.1 g of 1-(4-chlorophenyl)-3-[4-(2-methoxyethyl)piperazine-1-yl]methyl-2-pyrrolidinone.

Melting point: 103–105° C.;
$^1$H-NMR (CDCl$_3$, δ ppm): 2.01–2.12 (1H,m), 2.29–2.62 (12H,m), 2.78–2.94 (2H,m), 3.35 (3H,s), 3.51 (2H,t), 3.74–3.80 (2H,m), 7.32 (2H,d), 7.59 (2H,d).

Reference Example 4
Production of 1-(4-bromophenyl)-3-[4-(2-methoxyethyl)piperazine-1-yl]methyl-2-pyrrolidinone 1.31 g of 1-(4-bromophenyl)-3-methylene-2-pyrrolidinone and 1.00 g of 4-(2-methoxyethyl)piperazine were mixed with 5 ml of ethylene glycol dimethyl ether. The mixture was refluxed for 6.5 hours and then cooled. Thereto was added water. The mixture was subjected to extraction with ethyl acetate twice. The organic layer was dried over anhydrous magnesium sulfate and then concentrated to obtain 1.91 g of 1-(4-bromophenyl)-3-[4-(2-methoxyethyl)piperazine-1-yl]methyl-2-pyrrolidinone.

$^1$H-NMR (CDCl$_3$, δ ppm): 1.98–2.12 (1H,m), 2.29–2.41 (1H,m), 2.53–2.63 (11H,m), 2.78–2.94 (2H,m), 3.35 (3H,s), 3.51 (2H,t), 3.74–3.82 (2H,m), 7.46 (2H,d), 7.54 (2H,d).

Reference Example 5
Production of 1-(4-bromophenyl)-3-[4-(2-methoxyphenyl)piperazine-1-yl]methyl-2-pyrrolidinone 1.31 g of 1-(4-bromophenyl)-3-methylene-2-pyrrolidinone and 2.00 g of 4-(2-methoxyphenyl)piperazine were mixed with 5 ml of ethylene glycol dimethyl ether. The mixture was refluxed for 2 hours and then cooled. Thereto was added water. The mixture was subjected to extraction with ethyl acetate twice. The organic layer was dried over anhydrous magnesium sulfate and then concentrated to obtain an oily material. The oily material was purified by silica gel column chromatography using a mixed solvent of chloroform/methanol=40/1 to obtain 1.88 g of oily 1-(4-bromophenyl)-3-[4-(2-methoxyphenyl)piperazine-1-yl]methyl-2-pyrrolidinone.

$^1$H-NMR (CDCl$_3$, δ ppm): 2.03–2.17 (1H,m), 2.34–2.46 (1H,m), 2.60–3.20 (11H,m), 3.70–3.89 (2H,m), 3.87 (3H,s), 6.85–7.04 (4H,m), 7.45–7.59 (4H,m).

Reference Example 6
Production of 1-(4-bromophenyl)-3-pyrrolidinomethyl-2-pyrrolidinone There were mixed 1.31 g of 1-(4-bromophenyl)-3-methylene-2-pyrrolidinone, 2.00 g of 4-(2-methoxyphenyl)piperazine and 5 ml of pyrrolidine. The mixture was refluxed for 1 hour and then cooled. Thereto was added water. The mixture was subjected to extraction with ethyl acetate twice. The organic layer was dried over anhydrous magnesium sulfate and concentrated. The residue was purified by silica gel column chromatography using a mixed solvent of chloroform/methanol=40/1 to obtain 1.79 g of 1-(4-bromophenyl)-3-pyrrolidinomethyl-2-pyrrolidinone.

hu 1H-NMR (CDCl$_3$, δ ppm): 1.74–1.84 (4H,m), 2.01–2.15 (1H,m), 2.34–2.45 (1H,m), 2.51–2.88 (6H,m), 2.94–3.00 (1H,m), 3.75–3.80 (2H,m), 7.46 (2H,d), 7.55 (2H,d).

What is claimed is:

1. A process for producing a pyrrolidinone compound represented by the formula (1):

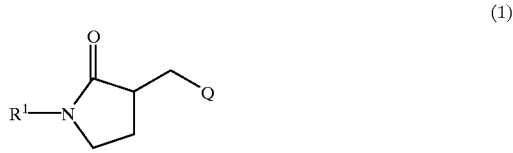

(1)

wherein R$^1$ is an alkyl group of 1 to 12 carbon atoms or a substituent represented by the formula (2):

(2)

(wherein R$^2$ is a hydrogen atom, a halogen atom, an alkyl group of 1 to 4 carbon atoms, an alkoxy group of 1 to 4 carbon atoms, a perfluoroalkyl group of 1 to 4 carbon atoms, a hydroxyl group, a cyano group, an amino group, a nitro group, a carbamoyl group, a thiol group, an thioalkyl group of 1 to 4 carbon atoms or a carboxyl group; p is an integer of 1 to 5; when p is 2 or more, each R$^2$ independently has the same definition as given above; and j is an integer of 0 to 2), and Q is a substituent represented by the formula (3a), (3b), (3c) or (3d):

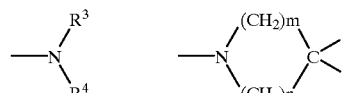
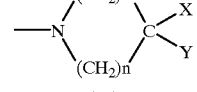

(3a)     (3b)

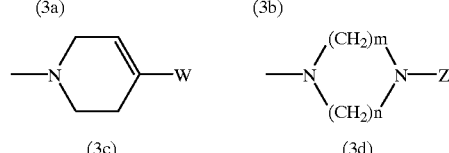

(3c)     (3d)

(in the formula (3a), R$^3$ and R$^4$ are each independently a hydrogen atom or an alkyl group of 1 to 4 carbon atoms, and $R^3$ and $R^4$ may bond to each other to form a morpholine ring; in the formula (3b), m and n are each independently an integer of 1 to 4, X is a hydrogen atom, a hydroxyl group, a cyano group, a carbamoyl group, a halogen atom or an alkyl group of 1 to 4 carbon atoms, and Y is a hydrogen atom, an alkyl group of 1 to 4 carbon atoms, a perfluoroalkyl group of 1 to 4 carbon atoms, a phenyl group or a phenyl group which is substituted with one or more groups or atoms selected from the group consisting of a halogen atom, an alkyl group of 1 to 4 carbon atoms, an alkoxy group of 1 to 4 carbon atoms and a perfluoroalkyl group of 1 to 4 carbon atoms; in the formula (3c), W is an alkyl group of 1 to 4 carbon atoms, a phenyl group or a phenyl group which is substituted with one or more groups or atoms selected from the group consisting of a halogen atom, an alkyl group of 1 to 4 carbon atoms, an alkoxy group of 1 to 4 carbon atoms and a perfluoroalkyl group of 1 to 4 carbon atoms, or an alkyl group of 1 to 2 carbon atoms substituted with a substituted or unsubstituted phenyl group; and in the formula (3d), m and n are each independently an integer of 1 to 4, Z is a hydrogen atom, an alkyl group of 1 to 18 carbon atoms, a phenyl group or a phenyl group which is substituted with one or more groups or atoms selected from the group consisting of a halogen atom, an alkyl group of 1 to 4 carbon atoms, an alkoxy group of 1 to 4 carbon atoms and a perfluoroalkyl group of 1 to 4 carbon atoms, an alkyl group of 1 to 2 carbon atoms substituted with a substituted or unsubstituted phenyl group, or a substituent represented by the formula (4):

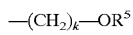
(4)

(wherein k is an integer of 2 to 3; and $R^5$ is a hydrogen atom, an alkyl group of 1 to 3 carbon atoms, an alkenyl group of 2 to 3 carbon atoms or an alkynyl group of 2 to 3 carbon atoms which process includes a step of reacting a compound represented by the formula (5):

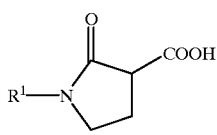
(5)

(wherein $R^1$ has the same definition as given above) with an amine derivative represented by the formula (6a), (6b), (6c) or (6d):

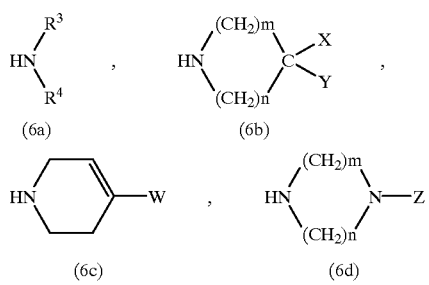

{in the formula (6a), $R^3$ and $R^4$ have the same definitions as given above; in the formula (6b), X, Y, m and n have the same definitions as given above; in the formula (6c), W has the same definition as given above; and in the formula (6d), Z, m and n have the same definitions as given above} in the presence of formaldehyde to produce a pyrrolidinone compound of the formula (1).

2. A process according to claim 1, wherein a pyrrolidinone compound of the formula (1) {wherein $R^1$ is a substituent represented by the formula (2a):

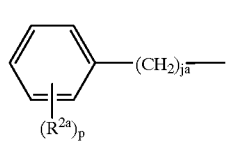
(2a)

(wherein $R^{2a}$ is a hydrogen atom or a halogen atom; p is an integer of 1 to 5; when p is 2 or more, each $R^{2a}$ independently has the same definition as given above; and $j^a$ is 0), and Q is a substituent represented by the formula (7):

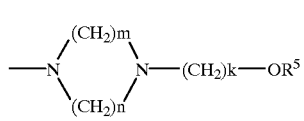
(7)

(wherein m and n are each independently an integer of 1 to 4; k is an integer of 2 to 3; and $R^5$ is a hydrogen atom, an alkyl group of 1 to 3 carbon atoms, an alkenyl group of 2 to 3 carbon atoms or an alkynyl group of 2 to 3 carbon atoms)} is produced by reacting a compound of the formula (5) {wherein $R^1$ is a substituent represented by the formula (2a) (wherein $R^{2a}$, p and $j^a$ have the same definitions as given above)} with an amine derivative represented by the formula (6d) {wherein Z is a substituent represented by the formula (4) (wherein k and $R^5$ have the same definitions as given above)} in the presence of formaldehyde.

3. A process according to claim 2, wherein a pyrrolidinone compound of the formula (1) {wherein $R^1$ is a 4-chlorophenyl group and Q is a substituent represented by the formula (8):

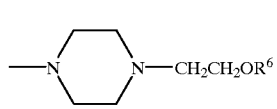
(8)

(wherein $R^6$ is an alkyl group of 1 to 3 carbon atoms)} is produced by reacting a compound of the formula (5) (wherein $R^1$ is a 4-chlorophenyl group) with an amine derivative represented by the formula (9):

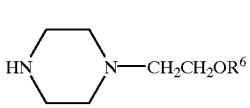
(9)

(wherein $R^6$ has the same definition as given above) in the presence of formaldehyde.

4. A process according to claim 3, wherein the amine derivative is a compound of the formula (9) wherein $R^6$ is a methyl group.

* * * * *

UNITED STATES PATENT AND TRADEMARK OFFICE
CERTIFICATE OF CORRECTION

PATENT NO.    : 6,207,825 B1
DATED         : March 27, 2001
INVENTOR(S)   : Hajime Iizuka et al.

It is certified that error appears in the above-identified patent and that said Letters Patent is hereby corrected as shown below:

<u>Title page,</u>
Item [73], please change the Assignee from "Mitsui Chemicals, Inc. (JP)" to -- Schering Aktiengesellschaft (DE) --.

Signed and Sealed this

Seventeenth Day of September, 2002

Attest:

JAMES E. ROGAN
Attesting Officer    Director of the United States Patent and Trademark Office